United States Patent [19]

Davies

[11] Patent Number: 4,990,676

[45] Date of Patent: Feb. 5, 1991

[54] PROCESS FOR PREPARING CHIRAL SULPHOXIDES

[75] Inventor: Stephen G. Davies, Oxford, England

[73] Assignee: British Petroleum Company p.l.c., London, England

[21] Appl. No.: 311,819

[22] Filed: Feb. 17, 1989

[30] Foreign Application Priority Data

Feb. 24, 1988 [GB] United Kingdom ............... 8804339
Nov. 8, 1988 [GB] United Kingdom ............... 8826144

[51] Int. Cl.$^5$ ........................................... C07C 315/04
[52] U.S. Cl. ....................................... 568/27; 556/16; 556/30
[58] Field of Search .................. 568/27; 556/30, 16

[56] References Cited

U.S. PATENT DOCUMENTS 3,280,017 10/1966 Hubel et al. .................... 556/30

OTHER PUBLICATIONS

D. Hwang et al., J. Org. Chem. (1985), vol. 50, pp. 1264–1271.
T. Flood et al., Chem. Abstracts, vol. 85, No. 63144a (1976).
L. Weber, Chem. Abtracts, vol. 86, No. 89989a (1977).
Pitchen, P. et al., "An Efficient Asymmetric . . . " J. Am. Chem. Soc. 1984 106, pp. 8188–8193.
Di Furia, R., et al., "Synthesis of Chiral Sulphoxides . . . " Communications, Apr. 1984, pp. 325–326.

*Primary Examiner*—Mary E. Ceperley
*Attorney, Agent, or Firm*—Nixon & Vanderhye

[57] ABSTRACT

A process for preparing single enantiomers of chiral sulphoxides is provided. The process involves (a) reacting an achiral sulphur-containing, e.g. a disulphide, with a single enantiomer of a chiral template having the formula T—(CO)—$CH_2R^1$, wherein T is suitably (eta-$^5$—$C_5H_5$)Fe(CO)(PPh$_3$)— (Ph=phenyl) and (b) thereafter sterospecifically oxidizing the sulphur atom with an oxidizing agent. A single enantiomer of the chiral sulphoxide can then be generated by reacting the oxidized product with a carbanion. In a preferred embodiment the reaction mixture is thereafter treated with further achiral sulphide to provide a process which is catalytic on the chiral template.

7 Claims, No Drawings

PROCESS FOR PREPARING CHIRAL SULPHOXIDES

The present invention relates to the selective formation of single enantiomers of chiral sulphoxides from sulphur compounds such as achiral disulphides.

Chemical compounds may be divided into two catagories, those compounds having molecular structures (isomers) which are superimposable upon their mirror images and those which do not. The former category are called achiral molecules and the latter are called chiral molecules. In one type of chiral molecule, the chirality arises as a consequence of the molecule possessing one or more chiral centres. Such chiral centres arise as a consequence of a non-symmetric disposition of functional groups or ligands at a particular point in the molecule. Thus in the case of the molecule lactic acid (2-hydroxypropanoic acid), the molecule has a single chiral centre, the carbon atom bonded to the hydroxyl group, and the chirality arises as a consequence of the tertrahedral disposition of four non-equivalent functional groups about this atom.

For chiral molecules possessing more than one chiral centre the situation is more complicated since each chiral centre introduces two possible non-superimposable structure elements into the molecule. Hence, for such molecules there exists a maximum of $2^n$ isomers of the molecule corresponding to the various permutations of the non-superimposable structure elements.

For molecules having one chiral centre, as in the case of lactic acid, the two non-superimposable isomers of the molecule are mirror images of each other. Such mirror image forms, which are equivalent to the right and left hands of a pair of gloves, are called enantiomers. In the case of molecules having more than one chiral centre, some paris of non-superimposable forms are mirror images and hence are enantiomers of each other while other pairs are not. Pairs of non-superimposable isomers which are not mirror images of each other are called diastereoisomers. In general a molecule having a n chiral centres will have a maximum of $2^n$ isomers consisting of $2^{n-1}$ pairs of enantiomers with each pair of enantiomers being diastereoisomers of all the other pairs.

Attempts to prepare chiral molecules by standard chemical methods usually lead to the formation of a product consisting of a mixture of all the non-superimposable isomers without enantiometric selectivity. Thus if a particular enantiomer or pair of enantiomers is required, as for example in a pharamaceutical application where often only one enantiomer is biologically active, it is necessary to separate or resolve the mixture into the individual isomers.

The need to separate individual enantiomers of chiral molecules from mixtures presents a major obstacle to the exploitation of such molecules on a large scale. Although mixtures of enantiomers and distereoisomers can be resolved into racemic mixtures of enantiomeric pairs, separation of single enantiomers from such racemic mixtures is difficult because, the enantiomers in a given pair of diastereoisomers always have identical chemical properties and hence cannot be separated by a selective chemical reaction unless a chiral organic substrate is used. Even in these cases, however, it is still necessary to use expensive techniques such as fractional crystallization which are difficult to operate on a large scale. For such reasons, exploitation of the properties of chiral molecules has only previously occurred where a particular enantiomer can be synthesized selectively by using a biological agent such as an enzyme.

A new process has been developed which makes it possible to prepare single enantiomers of chiral sulphoxides starting from a substrate comprising a achiral reactive sulphur compound e.g., an achiral symmetric disulphide. It is a feature of the new process that the chirality is introduced by first reacting the substrate with a single enantiomer of chiral template and thereafter using the chirality of the template to introduce chirality into the substrate during an oxidation stage with enantiomeric selectivity. It is a further feature of the new process that, after the oxidation stage, the chiral template can be regenerated in its single enantiomeric form whilst at the same time liberating a single enantiomer of the chiral sulphoxide. The overall process is therefore catalytic on the chiral template.

An important step in the new process is the reaction of a single enantiomer of the molecule

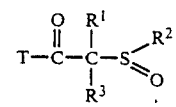

wherein
(a) T is the moiety (Cp)Fe(CO)(Z)—where Cp is (eta$^5$—C$_5$H$_5$) or a C$_1$ to C$_3$ alkyl substituted derivative thereof,
(b) Z is a ligand having the formula (R$^4$)$_2$X R$^5$ in which X is either phosphorus or arsenic, the R$^4$ groups are either phenyl or phenoxy groups and R$^5$ is selected from phenyl or phenoxy groups, functionalized or unfunctionalized C$_1$ to C$_{12}$ alkyl group, or alkoxy groups,
(c) R$^1$ and R$^2$ are independently selected from C$_1$ to C$_{12}$ alkyl, C$_6$–C$_{10}$ aryl or vinyl groups, and
(d) R$^3$ is selected from hydrogen, C$_1$ to C$_{12}$ alkyl, C$_6$ to C$_{10}$ aryl or vinyl groups, with a carbanion of formula R$^-$ where R is any organic radical.

According to the present invention therefore there is provided a process for making a single enantiomer of a sulphoxide having the formula

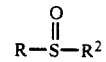

which process comprises reacting a single enantiomer of the molecule

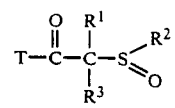

(wherein T, R$^1$, R$^2$ and R$^3$ are as defined above) with a source of a carbanion of formula R$^-$ where R is any organic radical.

Considering further the moiety T, the group Cp is preferably selected from cyclopentadienyl (C$_5$H$_5$), pentamethylcyclopentadienyl (C$_5$(CH$_3$)$_5$) or any of the other methyl substituted cyclopentadienyls. The Cp group is bonded eta$^5$ onto the iron atom.

The ligand having the formula $(R^4)_2XR^5$ is preferably one in which X is phosphorus. The $R^4$ groups are suitably either phenyl or phenoxy or $C_1$ to $C_6$ alkyl substituted phenyl or phenoxy. Most preferably the $R^4$ groups are both phenyl groups or both phenoxy groups or one phenyl and one phenoxy group. The $R^5$ group is preferably selected from the group consisting of preferred $R^4$ groups or $C_1$ to $C_{10}$ alkyl or alkoxy groups. In the case where $R^5$ group is either a $C_1$ to $C_{10}$ alkyl or alkoxy group, it is preferred that the alkyl or alkoxy groups is a $C_4$ to $C_{10}$ cycloalkyl or cycloalkoxy group. Most preferred are the ligands triphenylphosphine, diphenylcyclohexylphosphine, triphenylphosphite and diphenylcyclohexylphosphite.

The $R^1$ and $R^2$ groups are preferably selected from the group consisting of $C_1$ to $C_4$ alkyl groups, phenyl groups or vinyl groups. Likewise, $R^3$ is preferably selected from hydrogen, $C_1$ to $C_4$ alkyl groups, phenyl of vinyl.

In a preferred embodiment the carbanion $R^-$ is reacted with a molecule having the formula:

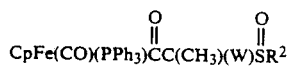

wherein W is either H or $CH_3$ and Cp is cyclopentadienyl.

The carbanion is preferably one in which R is $C_1$ to $C_{10}$ alkyl or $C_6$ to $C_{12}$ aryl. A source of such carbanions includes for example metal alkyls, e.g., alkali metal alkyls such as lithium alkyls and sodium alkyls, or alkali metal copper alkyls, such as those having the formula $LiCuR_2$.

The reaction is preferably carried out in a dry, unreactive solvent (e.g., an ether such as THF) at a temperature below room temperature. It is also preferred to carry out the reaction under an inert atmosphere for example a gas such as nitrogen, argon, helium and the like. After the reaction has occurred the product can be purified by standard techniques such as filtration, liquid-liquid extraction and chomatography.

In an embodiment of the present invention the substrate is prepared by stereospecific oxidation of the corresponding single enantiomer of the sulphide having the formula:

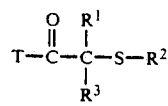

It has been found that oxidation of the above sulphide can occur with almost 100% stereoselectivity even when an achiral oxidizing agent is employed.

According, therefore, to an embodiment of the present invention there is provided a process for preparing a single enantiomer of a sulphoxide having the formula:

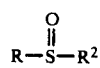

which process comprises the steps:
(1) reacting a single enantiomer of the sulphide:

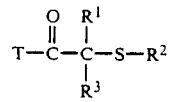

wherein T, $F^1$, $F^2$ and $R^3$ are as defined previously, with an oxidizing agent to produce the corresponding enantiomer of the substrate

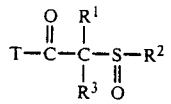

and
(2) thereafter reacting the corresponding enantiomer of the substrate with a carbanion of formula $R^-$ in the manner previously defined.

The oxidizing agent is suitably a peracid, a peroxide or a hydroperoxide. A preferred oxidizing agent is meta-chloroperbenzoic acid. It is preferable to carry out the oxidation in a solvent at a temperature suitably below $-20°$ C., preferably below $-50°$ C.

It will be appreciated that if a chiral oxidizing agent is used, for example those disclosed in J. Amer. Chem. Soc. 1984 106 p8188 or in Synthesis 1984 p525 (e.g., $Ti(O-iC_3H_7)_4/(+)$ or $(-)$ diethyl tartrate/$H_2O$/$t-C_4H_9OOH$ it is possible to selectively oxidize one of the enantiomers of the sluphide in a racemic mixture of such species. According therefore to a further embodiment of the present invention, there is provided a process for preparing a single enantiomer of a sulphoxide having the formula

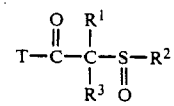

which process comprises treating a racemic mixture of the enantiomers of a sulphide having the formula

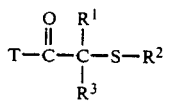

with a chiral oxidizing agent.

These oxidation processes are suitably carried out under an inert atmosphere below room temperature as defined above.

The sulphide defined above can be produced by the following process. The first stage of this process comprises treating the enolate of a single enantiomer of the complex

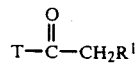

with an achiral sulphur compound preferably an achiral sulphur-containing compound having the formula $R^2-S-X$ where X is a leaving group such as $-SR^2$, $-SO_2R^2$, $-Cl$, $-Br$, etc. which can be displaced by an enolate. In practice, this can be achieved by first reacting the complex with an agent such as alkali metal alkyl, which converts the complex into its corresponding enolate, and thereafter treating the enolate with the achiral disulphide. The addition of the achiral sulphur-containing compound also stereoselective. For example, treatment of (R, S) CpFe(CO)(PPh$_3$)(COCH$_2$CH$_3$) with diphenyl sulphide produces a 16:1 mixture of the (RS, SR) and (RR, SS) diastereoisomers.

The product of the first stage, which has the formula:

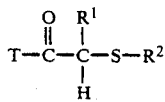

can be oxidized to the corresponding sulphoxide using the process defined above. Alternatively this product can be converted into another sulphide by deprotonation and subsequent treatment with a compound which adds an R$^3$ group to the carbon atom located alpha to the sulphur. The compound is suitably an alkylating, acylating or vinylating agent. A preferred alkylating agent is an alkyl halide, e.g., an alkyliodide. It will be appreciated that this second stage of the process can be performed after the oxidation of the sulphide to sulphoxide if desired.

The complex defined above can be readily produced from a precursor having the formula

by first forming the corresponding enolate and thereafter treating the enolate with an organic halide of formula R$^1$Y, where Y is preferably an iodide.

Using the sequences of reactions described above, it is possible to produce enantiomerically pure chiral sulphoxides from chiral symmetric disulphides.

Finally, it has been observed that if the single enantiomer of the substrate is treated first with a carbanion of formula R$^-$ and thereafter with an achiral sulphur-containing compound having the formula R$^2$—S—X, where X is a leaving group such as —SR$^2$, —SO$_2$R$^2$, —Cl, —Br etc., then the corresponding single enantiomer of the sulphide having the formula:

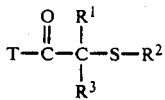

is regenerated. Thus the present invention also provides a catalytic cycle, involving single enantiomers of the substrate and sulphide by means of which an achiral sulphur-containing compound can be selectively oxidized to one of the enantiomers of a corresponding chiral sulphoxide.

It has further been found that a single enantiomer of an optically active sulphoxide of formula:

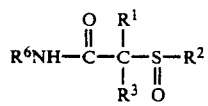

can be prepared by reacting a single enantiomer of the molecule:

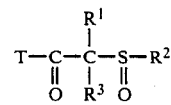

with an N-Halosuccinimide (e.g., N-bromosuccinimide) and an amine of formula R$^6$NH$_2$ wherein R$_6$ is selected from C$_1$ to C$_{20}$ alkyl, or C$_6$–C$_{20}$ aryl, aralkyl or alkaryl. The reaction is suitably carried out under an inert atmosphere below room temperature.

The invention is now illustrated with reference to the following Examples.

EXPERIMENTAL DETAILS

All reactions and purifications were performed under nitrogen atmosphere using standard vacuum line and Schlenk tube techniques. Removal of all solvents was carried out under reduced pressure. THF was dried over sodium benzophenone ketyl and distilled. Dichloromethane was distilled from calcium hydride and hexane refers to that fraction boiling in the range 67°–70° C. n-Butyllithium (2.5 M in hexane or 1.65 M in hexane) and tert-butyllithium (1.4 M in pentane) were used as supplied by Aldrich. All melting points were recorded on a Gallenkamp melting point apparatus and are uncorrected. IR spectra were recorded in dichloromethane on a Perkin-Elmer 297 instrument. Proton nmr spectra were recorded on a Bruker WH300 spectrometer at 300.13 MHz or in a Varian Gemini —200 at 200.0 MHz and referenced to residual protio-solvent, with chemical shifts being reported as ppm from (CH$_3$)$_4$Si. Carbon-13 nmr spectra were recorded on a Bruker AM250 spectrometer at 62.90 MHz using CDCl$_3$ as solvent and internal standard and are reported as ppm from (CH$_3$)$_4$Si. Phosphorous-31 nmr spectra were recorded at 101.26 MHz using CDCl$_3$ as solvent and are reported as ppm from an external reference of triethylphosphate in D$_2$O. Electron impact mass spectra were recorded on either a VG micromass ZAB2F instrument or a VG Masslab 20-250 instrument using EI and FD techniques. Chemical ionisation mass spectra were recorded on a VG Masslab 20-250 instrument using ammonia as the reagent gas. Optical rotations were recorded on a Perkin-Elmer 241 polarimeter. Elemental analyses were performed by the Dyson Perrins Laboratory Analytical Service (Oxford, UK).

EXAMPLE 1 - Preparation of (RS, SR)-[(eta$^5$—C$_5$H$_5$)Fe(CO)(PPh$_3$) COC(CH$_3$)$_2$SOPh](RS, SR)-2)

n-Butyllithium (0.67 ml, 1.1 mmol) was added dropwise to a solution of hexamethyldisilazane (0.27 ml, 1.3 mmol) in THF (20 ml) at 0° C. After 15 minutes the resulting solution of lithium hexamethyldisilazide was added dropwise to a stirred solution of (RSS, SRR)(eta$^5$—C$_5$H$_5$)Fe(CO)(PPh$_3$)COCH(CH$_3$)SOPh-1 (0.275 g, 0.46 mmol) in THF (30 ml) at −78° C. The solution rapidly turned from orange to red and after 1 hour at −78° C. excess methyl iodide (0.50 ml, 7.9 mmol) was injected into the reaction Schlenk. The solution was stirred at −40° C. for 4 hours, quenched with methanol, and then filtered through a plug of alumina (Grade V). Volatiles were removed under vacuum and removed and the crude product was chromatographed on alumina (Grade V) to afford an orange-red band (dichloromethane elution) of (RS, SR)-2. Recrystallization from dichloromethane/heptane afforded spectroscopically pure material as a light orange microcrystalline solid (0.247 g, 89%). $\delta^1$H NMR (CDCl$_3$, 200 MHz): $\delta$7.7-7.3 (2OH, c, Ph), 4.53 (5H, d, J$_{P-H}$ =1.1 Hz, C$_5$H$_5$), 1.41 (3H, s, CH$_3$), 0.18 (3H, S CH$_3$).

EXAMPLE 2 - Preparation of (R, S)-[(eta$^5$—C$_5$H$_5$)Fe(CO)(PPh$_3$)CO(CH$_3$)$_2$SPh]((R, S)-3) and (R, S)-(p-Tol)PhSO A solution of (p-Tol)Li (1.0 ml, 0.32 mmol;Tol=tolyl) in 10 ml THF was treated with 0.23 ml (1.5 mmol) TMEDA and the resulting mixture slowly dripped into a THF solution (30 ml) of (RS, SR)-2 (0.195 g, 0.32 mmol) cooled to −78° C. The reaction mixture rapidly became a deep purple and, after 15 minutes, was quenched with three equivalents of phenyl disulphide (0.218 g, 1.0 mmol) in THF (10 ml). The resulting orange solution was stirred for an additional 10 minutes at −78° C. and then warmed to room temperature and passed through a plug of alumina (Grade V). Volatiles were removed under vacuum, and the crude oily orange products were chromatographed on alumina (Grade IV) to afford an orange-red band (40:60 petrol/dichloromethane, 3:1 elution) of (R, S)-3 (0.145 g, 77% upon vacuum removal of solvent), and a light yellow band (dichloromethane elution) of (R, S)-(p-Tol)PhSO. The sulphoxide was purified by preparative TLC (dichlormethane/ether, 9:1 elution) to give 35 mg (50%) of a colourless oil. $\delta^1$H NMR of (R, S)-3 (CDCl$_3$, 200 MHz): 7.7-7.2 (2OH), c, C$_6$H$_5$), 4.48 (5H, s, C$_5$H$_5$), 2.0 (3H, s, CH$_3$), 0.73 (3H, s, CH$_3$).$\delta^1$H NMR of (p-Tol)PhSO (CDCl$_3$, 300 MHz): 7.8-7.6 (2H, m, C$_6$H$_5$), 7.6-7.4 (5H, c, C$_6$H$_5$+CH$_3$C$_6$H$_4$), 7.3-7.2 (2H, d of d, J+ 8/5. 2.1 Hz, CH$_3$C$_6$H$_5$), 2.36 (3H, s, CH$_3$). Mass spectrum of (p-Tol)PhSO, parent ion: m/e+216.

EXAMPLE 3 - Stereoselective Oxidation of (R, S)-3

A 20 ml THF solution of (R, S) (0.12 g, 0.20 mmol) was cooled to −78° C. and slowly dripped into a solution of meta-chloroperbenzoic acid (0.060 g, 0.35 mmol) in THF (10 ml) at −100° C. over 45 minutes. After addition, the reaction was shown to be complete by TLC (Merck A1 sheets, silica gel 60 F$_{254}$, dichloromethane/ether 9:1 elution) and solvent was removed under vacuum. The crude orange product was chromatographed on alumina (Grade IV) to give a red-orange band (dichloromethane elution) of (RS, SR)-2 (0.104 g, 86%, upon vacuum removal of solvent).

EXAMPLE 4 - PREPARATION OF (R, S)-[(eta$^5$—C$_5$H$_5$)Fe(CO)(PPh$_3$) COCH(CH$_3$)SPh]

n-Butyllithium (1.90 ml, 4.66 mmol) was added to a solution of (R)-[(eta$^5$—C$_5$H$_5$)Fe(CO)(PPh$_3$)COCH$_2$CH$_3$] (1.986 g, 4.24 mmol) in THF (50 ml) at −78° C. and stirred for 1 hour. A solution of diphenyl disulphide (1.11 g, 5.09 mmol) in THF (10 ml) was then added to the reaction mixture which was stirred at −78° C. for a further 1 hour. The resulting khaki solution was quenched with methanol and allowed to warm to room temperature, before being concentrated and filtered through alumina (Grade V). The crude product was chromatographed on flash silica to give an orange band (dichloromethane:40/60 petrol, 4:1 elution) of (R, S)-[(eta$^5$—C$_5$H$_5$)Fe(CO)(PPh$_3$)COCH(CH$_3$)SPh] (1.62 g, 66%) followed by a faint yellow band of (R, R)[(eta$^5$—C$_5$H$_5$)Fe(DO)(PPh$_3$)COCH(CH$_3$)SPh] (0.20 g, 8%). The major (R, S)-diastereoisomer was recrystallized from dichloromethane/heptane to afford orange prisms; (Found C 69.0; H 5.1; P 5.4; S 5.4. C$_{33}$H$_{29}$FeO$_2$PS requires C 68.8; H 5.1; P 5.4; S 5.6%); [α]$_D$$^{20}$-275, [α]$_{578}$$^{20}$-310, [α]$_{546}$$^{20}$-439 (c 0.067, C$_6$H$_6$); $\nu_{max}$. cm$^{-1}$1928s (C≡O), 1590s cm$^{-1}$ (C≡O);$\delta^1$Hnmr 7.57-7.19 (2OH, complex m, Ph), 4.47 (5H,J$_{PH}$ 1.3 Hz, C$_5$H$_5$), 4.18 (1H,q,J$_{2,3}$6.7 Hz,CHCH$_3$), 0.62(3H,d,J$_{2,3}$6.7 Hz, CHCH$_3$); $^{13}$Cnmr 272.66 (d,$^2$J$_{PC}$23.6 Hz, C≡O), 220.66(d,$^2$J$_{PC}$29.9 Hz, C≡O), 136.37(d,$^1$J$_{PC}$42.9 Hz,Ph C$_{ipso}$), 136.34 (s, SPh C$_{ipso}$), 133.42(d,$^2$J$_{PC}$9.2 Hz,Ph C$_{ortho}$), 131.55 (s) and 129.76 (s,SPh C$_{ortho}$ and C$_{meta}$), 128.71 (s,Ph C$_{para}$), 128.05 (d,$^e$J$_{PC}$9.2 Hz,Ph C$_{meta}$), 126.39 (s,SPh C$_{para}$), 85.49 (s,C$_5$H$_5$), 70.99 (d,$^3$J$_{PC}$6.3 Hz, CHCH$_3$), 16.52 (s,CHCH$_3$); $^{31}$P($^1$H)nmr 70.83; m/z 576 (M+).

EXAMPLE 5 PREPARATION OF (R,S,S)-[(eta$^5$—C$_5$H$_5$)Fe(CO)(PPh$_3$) COCH(CH$_3$)SOPH]

A solution of (R, S)-[(eta$^5$—C$_5$H$_5$)Fe(CO)(PPh$_3$)COCH(CH$_3$)SPh$\pi$ (3.6 g, 6.32 mmol) in THF (100 ml) was cooled to −78° C. and added dropwise to a stirred solution of meta-chloroperbenzoic acid (1.36 g, 7.90 mmol) in THF (150 ml) maintained at −100° C. The resulting yellow solution was stirred at −100° C. for 3 hours before being allowed to warm slowly to room temperature and then concentrated. The crude product was chromatographed on alumina (Grade V) to yield a trace of unreacted starting material (dichloromethane elution) followed by a major orange band (dichloromethane:ethyl acetate, 17.3 elution) of (R,S,S)-[(eta$^5$—C$_5$H$_5$)Fe(CO)(PPh$_3$)COCH(CH$_3$)SOPh] (3.72 g, 99%). Recrystallization from dichloromethane/heptane afforded analytically pure material as orange masses (Found C 60.45; H 4.82. C$_{33}$H$_{29}$FeO$_3$PS.CH$_2$Cl$_2$ requires C 60.29; H 4.61%); [α]$_D$$^{20}$-338, [α $_{578}$$^{20}$-376, [α]$_{546}$$^{20}$-500 (c 0.05 C$_6$H$_6$); $\nu_{max}$. 1910s cm$^{-1}$(C≡O), 1590s cm$^{-1}$ (C≡O); $^1$Hnmr 7.62-7.57 (6H, m, Ph), 7.48-7.43 (5H, m, Ph), 7.42-7.27 (9H, m, Ph), 4.60 (5H, d, J$_{PH}$ 1.3 Hz, C$_5$H$_5$), 4.16 (1H, q, J$_{2, 3}$7.1 Hz, CHCH$_3$), 0.28 (3H, d, J$_{2, 3}$7.1 Hz, CHCH$_3$); $^{13}$Cnmr 273.05 (d,$^2$J$_{PC}$21.8 Hz, C≡O), 2220.10 (d,$^2$J$_{PC}$30.3 Hz, C≡O), 143,53 (s,SOPh C$_{ipso}$), 136,18 (d,$^1$J$_{PC}$42.8 Hz,Ph C$_{ipso}$), 133.56 (d,$^3$J$_{PC}$9.2 Hz, Ph C$_{meta}$), 130.84 (s,SOPh C$_{para}$), 129.70 (s), 128.67 (s) and 125.59 (s,Ph C$_{para}$, SOPh C$_{ortho}$ and C$_{meta}$), 127.93 (d,$^2$J$_{PC}$10.1 Hz,Ph C$_{ortho}$), 89.40 (d,$^3$J$_{PC}$5.3 Hz, CHCH$_3$), 86.08 (s, C$_5$H$_5$), 9.63 (s, CHCH$_3$); $^{31}$P($^1$H)nmr 70.96; m/z 592 (M+).

EXAMPLE 6 - REACTION OF LITHIUM di-n-BUTYLCUPRATE WITH (R,S,S)-[(eta$^5$—C$_5$H$_5$)Fe(DO)(PPh$_3$)-COCH(CH$_3$)SOPh]

n-Butyllithium (0.49 ml of a 2.5 M solution, 1.23 mmol) was added to a suspension of freshly precipitated cuprous iodide (0.128 g, 0.67 mmol) in THF (15 ml) at −40° C. and stirred for 15 minutes. To the resulting dark purple solution of lithium di-n-butylcuprate was then rapidly added on one portion a solution of (R,S,S)-[(eta$^5$—C$_5$H$_5$)Fe(CO)(PPh$_3$)COCH(CH$_3$)SOPh] (0.333 g, 0.56 mmol) in THF (15 ml) and stirred at −40° C. for a further 10 minutes. The reaction mixture was then quenched with methanol and allowed to warm to ambient temperature before being concentrated (ca 20° C.) and filtered through alumina (Grade V, dichloromethane:ethyl acetate, 1:1 elution). The crude product was dissolved in methanol (10 ml) and then diluted with distilled water (10 ml) to reprecipitating the iron containing components. The supernatant liquid was removed by filtration, and the above liquid-liquid extraction then repeated.

The combined aqueous methanol filtrates were concentrated (ca 20° C.) to give a pale orage oil. This material was applied to ptlc (dichloromethane:ether, 4:1 elution) to afford (R)-phenyl n-butyl sulphoxide (0.053 g, 96% yield based on a 55% conversion as determined by $^1$Hnmr analysis of the crude reaction mixture) as a near colourless oil. Cup distillation (bp 80°-85° C/0.4 mmHg, bp 99°-99.5° C./0.4 mmHg) gave pure sulphoxide (0.0364 g, 65% yield based on a 55% conversion) as a colourless liquid; $[\alpha]_D^{20}+181.0$ (c 9.42, EtOH), $[\alpha]_D^{20}+165.3$ (c 3.86, EtOH), $[\alpha]_D^{20}+177.1$ (c 5.14, EtOH). The spectral data recorded for this material were identical in all respects with those obtained for an authentic sample prepared by the method of Harpp et al (J. Org.chem 3987 41 (1976)). The optical purity of this material was confirmed by $^1$Hnmr analysis using the chiral shift reagent (−)-2,2,2-trifluoro-1-(9-anthryl)ethanol.

The precipitated iron containing components were applied to flash silica chromatography to give three orange bands. The first band (dichlormethane elution) yielded (R)—[(eta$^5$C$_5$H$_5$)Fe(DO)(PPh$_3$)COCH$_2$CH$_3$] (0.140 g, 55%). The second band (dichloromethane:ether, 7.3 elution) gave unreacted (R,S,S)[(eta$^5$—C$_5$H$_5$)Fe(CO)(PPh$_3$)COCH(CH$_3$)SOPh] (0.120 g, 36%). The third band (dichloromethane:ether, 1:1 elution) afforded (R, X, S)[(eta$^5$—C$_5$H$_5$)Fe(CO)(PPh$_3$)COCH(CH$_3$)SOPh] (0.0210 g, 6%). The specific rotations and $^1$Hnmr data obtained for these three products were identical in all respects to those described above.

EXAMPLE 7 - PREPARATION OF (S, S)-PhCH$_2$NHCOCH(CH$_3$)SOPh

A solution of N-Bromosuccinimde (0.077 g, 0.43 mmol) in dichloromethane (3 ml) was added dropwise to a stirred solution of (R,S,S)-[eta$^5$—C$_5$H$_5$)Fe(CO)(PPh$_3$)COCH(CH$_3$)SOPh] (0.2155 g, 0.36 mmol) and benzylamine (0.43 ml, 0.40 mmol) in dichloromethane (10 ml) maintained at −40° C. The orange solution was stirred at −40° c. for 30 min before being allowed to warm slowly to ambient temperature. The resulting dark green solution was stirred at ambient temperature for a further 4h and then concentrated in vacuo (ca. 20° C.). The crude product was purified by p.t.l.c. (dichloromethane:ether, 17:3 elution) to afford (S, S)-PhCH$_2$NHCOCH(CH$_3$)SOPh (0.0933 g, 90%) as an off-white solid. Recrystallization from dichloromethane/heptane yielded fine white crystals (0.0613 g, 59%), (Found C66.76; H5.77; N4.73; S11.07. C$_{16}$H$_{17}$NO$_2$S requires C66.87; H5.96; N4.87;S11.16%); m.p. 108.2°14 109.2° C.; $[\alpha]_D^{20}$-184, $[\alpha]_{578}^{20}$-227 (c4.77EtOH), the optical purity of this material has been confirmed by 300 MHz $^1$H n.m.r. analysis using the chiral shift reagent (−) -2,2,2-trifluoro-1-(9-anthryl) ethanol; max 3420 w (N-H), 3290 m (N—H), 1668s (C=O), 1520 m cm$^{-1}$ (aromaatic C=C); $^1$H n.m.r. 7.20-7.54 (11H, complex m, Ph and NH), 4.35 (2H,dABq,JAB14.7 Hz and JCH,NH5.9 Hz,PhCH$_2$), 3.42 (1H, q, J2, 3 7.4 Hz, CHCH$_3$), 1.61 (3H, d, J2, 3 7.4 Hz, CHCH$_3$); 13C n.m.r. 167.61 (s, C=O), 140.52 (s, PhC$_{ipso}$), 137.75 (s, Ph C$_{ipso}$), 131.49(d), 129.20(d), 128.61(d), 127.91 (d), and 124.54 (d, Ph C$_{ortho}$, C$_{meta}$ and C$_{para}$), 62.40 (d, CHCH$_3$), 43.53 (t,PhCH$_2$), 13.12 (q, CHCH$_3$); CIMS (NH$_3$) 288(MH+,100%).

I claim:
1. A process for preparing a single enantiomer of a sulphoxide having the formula:

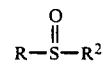

which comprises reacting a single enantiomer of the molecule:

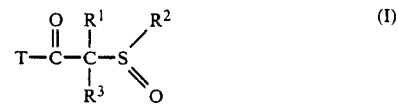

wherein
T is the moiety (Cp)Fe(CO)(Z)—where Cp is selected from (eta$^5$—CH$_5$H$_5$) and a C$_1$ to C$_3$ alkyl substituted derivative thereof;
Z is a ligand having the formula (R$^4$)$_2$X R$^5$ in which X is selected from phosphorus and arsenic, R$^4$ is selected from phenyl and phenoxy, and R$^5$ is selected from phenyl, phenoxy, C$_1$ to C$_{12}$ alkyl group and alkoxy;
R$^1$ to R$^2$ are independently selected from C$_1$ to C$_{12}$ alkyl, C$_6$-C$_{10}$ aryl and vinyl; and
R$^3$ is selected from hydrogen, C$_1$ to C$_{12}$ alkyl, C$_6$ to C$_{10}$ aryl and vinyl,
with a carbanion of formula F$^-$ where R is selected from C$_1$-C$_{10}$ alkyl and C$_6$-C$_{12}$ aryl.

2. A process as claimed in claim 1, wherein the single enantiomer of the molecule having the formula (I) is prepared by reacting a single enantiomer of the sulphide:

with an oxidizing agent.

3. a process as claimed in claim 2, wherein the single enantiomer of the sulphide having the formula (II) in which R$^3$ is hydrogen, is produced by reacting the enolate of a single enantiomer of the complex:

with an achiral sulphur-containing compound having the formula R$^2$—S—X where X is a leaving group selected from —SR$^2$ —SO$_2$R$^2$, —Cl and —Br.

4. A process as claimed in claim 2, wherein the single enantiomer of the molecule having the formula (II) and having R$^3$ other than hydrogen is produced by:
(a) in a first step reacting the enolate of a single enantiomer of the complex

with an achiral sulphur-containing compound having the formula R$^2$—S—X where X is a leaving group selected from —SR$^2$ —SO$_2$R$^2$, —Cl and —Br, (b) in a second step reacting the product of step (a) with an alkylating agent or an arylating agent or a vinylating agent.

5. A process as claimed in claim 3, wherein the single enantiomer of the complex of formula (III) is prepared by reacting the enolate of a precursor having the formula:

 (V)

with an organic halide of formula $F^1Y$.

6. A process as claimed in claim 4, wherein the single enantiomer of the complex of formula (III) is prepared by reacting the enolate of a precursor having the formula:

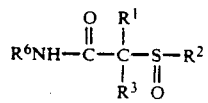

with an organic halid of formula $R^1Y$.

7. A process as claimed in claim 1, and further comprising the step of treating the product of the process of claim 1 with an achiral sluphur-containing compound having the formula $R^2-S-X$, wherein X is a leaving group selected from $-SR^2$, $SO_{2R}^2$, $-Cl$ and $-Br$, to thereby produce a single enantiomer of a sulphide having the formula (II),

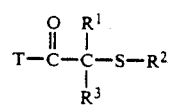 (II)

* * * * *